United States Patent [19]

Bischoff

[11] Patent Number: 4,742,228
[45] Date of Patent: May 3, 1988

[54] INFRARED MEASURING APPARATUS AND PROCESS FOR THE CONTINUOUS QUANTITATIVE DETERMINATION OF INDIVIDUAL COMPONENTS OF FLOUR OR OTHER GROUNDABLE FOOD PRODUCTS

[75] Inventor: Bruno Bischoff, St. Gallen, Switzerland

[73] Assignee: Gebrüder Bühler AG, Uzwil, Switzerland

[21] Appl. No.: 810,337

[22] PCT Filed: Apr. 15, 1985

[86] PCT No.: PCT/EP85/00170
§ 371 Date: Dec. 9, 1985
§ 102(e) Date: Dec. 9, 1985

[87] PCT Pub. No.: WO85/04957
PCT Pub. Date: Nov. 7, 1985

[30] Foreign Application Priority Data

Apr. 19, 1984 [CH] Switzerland ............... 1964/84
May 8, 1984 [CH] Switzerland ............... 2236/84
Nov. 15, 1984 [DE] Fed. Rep. of Germany ....... 3441856

[51] Int. Cl.⁴ ............................................. G01N 21/01
[52] U.S. Cl. ................................... 250/341; 250/304; 250/339; 250/359.1; 356/36
[58] Field of Search ............... 250/341, 340, 339, 304, 250/360.1, 359.1, 358.1, 356.1, 576; 356/38, 36; 73/169

[56] References Cited

U.S. PATENT DOCUMENTS 3,321,636 5/1967 Karrer ............................ 250/574
4,260,263 4/1981 Kummer ........................ 356/448
4,422,760 12/1983 Webster ......................... 356/244
4,479,055 10/1984 Perten .......................... 250/338
4,563,581 1/1986 Perten .......................... 250/338
4,640,614 2/1987 Roberts et al. .................. 356/36

FOREIGN PATENT DOCUMENTS

0061437 9/1982 European Pat. Off. .
2437621 8/1980 France .

Primary Examiner—Janice A. Howell
Assistant Examiner—Constantine Hannaher
Attorney, Agent, or Firm—Helfgott & Karas

[57] ABSTRACT

In an infrared measuring apparatus for the continuous quantitative determination of individual components of flour or other groundable food products in a tubular measurement segment (24) with forced transport (27) of the material to be measured, equipment (29, 31, 32, 33, 34) is provided for consolidating the material to be measured in the region of a sensor (20) for the measurement of the consolidated material. In the corresponding measurement process, the groundable product is passed over a measurement segment (24), a slight compression and smoothening of the groundable product being achieved in the region of the sensor (30). During cyclically repeated measurements, groundable product is compressed against the sensor (30), the groundable product is irradiated preferably in the infrared region and the protein content and/or water content (or also the ash content and/or the color value) of the test sample are determined with the aid of measuring equipment and a computer (38, 40) from the radiation (for example, light) reflected from the consolidated test sample to the sensor (30).

31 Claims, 10 Drawing Sheets

INFRARED MEASURING APPARATUS AND PROCESS FOR THE CONTINUOUS QUANTITATIVE DETERMINATION OF INDIVIDUAL COMPONENTS OF FLOUR OR OTHER GROUNDABLE FOOD PRODUCTS

TECHNICAL FIELD

The invention relates to an infrared measuring apparatus as well as to a process for the continuous quantitative measurement of components of flour or other groundable food products in a tubular measurement segment with forced transport of the material to be measured.

STATE OF THE ART ON WHICH THE INVENTION IS BASED

Infrared spectroscopy has already been used for some time in the grain processing industry for measuring various components (such as protein and water) in flour. These components exhibit a quite typical light-absorption and light-reflection behavior under infrared light.

On account of the natural factors of soil, climate and climate stability, very different grain harvests are a fact of life, especially, for example, in the European and adjoining areas. Also, with regard to grain production, other areas such as the USA, Canada and Australia are additionally privileged, not only owing to the fact that there are fewer climatic variations, but also because the soils and the climate permit the best qualities of grain to be produced, insofar as the bulk of the international grain trade is taken into consideration. Here also, as with many other goods, it is true that higher prices have to be paid for higher quality. In addition, there is the fact that each country attempts to keep as much as possible of the production of agricultural products in its own country. The consumer demands bread products, which correspond to his own concepts, whether they be taste, lightness, nutritional value, price, etc. The excesses and deficits are compensated for through international trade, however, with the disadvantage of widely varying qualities of the grain components. It becomes the task of the mill and the bakery (taking national interests into consideration) to optimize, so as to produce the best possible flour or bread with the largest possible proportion of cheap grain (low protein values, etc.) and the smallest possible proportion of expensive grain (high protein values, etc.)

At the present time, the market has the property that supply and price are subject to rapid changes, so that it is no longer acceptable for a mill to mix grain and add water according to the values of past experience. The market and, especially, the accounting point of view demand constant adaptation to existing conditions and this calls for the use of computers.

Extensive investigations and, especially, an examination in the laboratory of the best infrared measuring instruments known at the present time, led to the conclusion that the problems of laboratory measurement, but not those of continuous measurements during manufacture, can be regarded as solved.

In one respect, the handling of laboratory data is very simple; if the result deviates from reality, the measurement is repeated in ones' own or in an outside laboratory. However, the laboratory data can also be ignored and the manufacturing process continued, if all other data (including that obtained by sensory evaluation) suggests that such a course of action is justifiable. Man intervenes here with his decision.

In an investigations of the complex of problems, three "barriers", which are unsolved, have so far emerged:
1. With respect to its components (electronics etc.) laboratory mesauring equipment can be conceived for environmental influences of a lesser magnitude. If, however, laboratory measuring equipment is used in a manufacturing operation, the errors, which are caused by environmental influences, can in many cases not be separated from other malfunctions.
2. If a new system, such as infrared spectroscopy, which has been researched from a theoretical, and especially from a physical, chemical and mathematical point of view, is checked in the laboratory, and if the system, which has been recognized as usable, is subjected to the realities of use, it frequently turns out to be unfit for practical applications (that is, inexplicable errors and deviations occur).
3. Representative data for larger quantities of a product can frequently not be derived with sufficient reliability from practical measurements of individual samples.

DISCLOSURE OF THE INVENTIONS

It is an object of the invention to develop an apparatus and a process for continuously determining individual components of flour or other groundable food products, which avoid the disadvantages that have been described and, in particular, lead to representative test data, which, when employed in practical operations, are sufficiently reliable, so that the corresponding parameters can be controlled or regulated therewith in the processing. In this connection, the determination of the protein values, as well as of the water content of groundable products (especially of flour and floury products) stands in the foreground.

A secondary object of the invention is however also the possibility of simultaneously determining other parameters, such as the ash and the color of the groundable products.

This objective is accomplished inventively with an apparatus of the initially mentioned type, owing to the fact that equipment is provided in the measurement segment for consolidating the material to be measured in a region of a sensor for measuring the consolidated material.

Surprisingly, it has turned out that the invention has eliminated the listed "barriers" completely and overcome the problems arising from them.

For the invention, the product is brought into a slightly precompressed state in the measurement segment and then consolidated in the region of the sensor for the infrared measurement. With this, the preparation is deliberately carried out in two steps. At first, the product is subjected to a slight pressure so as to ensure that there no longer are any cavities in the product so that the flour at all times lies smoothly against the sensor or is even pressed slightly against it. With such a procedure, constant working conditions are created. It is well known that bulk materials and liquids are subject to significantly different laws. In the case of bulk materials, the mutual support of the particles is a characteristic feature that comes to the fore. The flour, slightly compressed by the forced transport, changes approximately into a lining, such as that, which is frequently used in laboratory equipment for measuring material properties. The flour no longer can "flow" in the forced transport space. A consolidation can therefore be produced locally in the flour. The consolidation is produced in the region of the sensor. Interfering "boundary conditions" are abolished, since the consolidation is produced within the same, slightly compressed flour and the air can escape. The test sample and the test conditions are optimum and reproducible from every point of view. The objective, on which the invention is based, can thus be realized, as already mentioned, in a surprisingly advantageous manner.

The invention permits various, particularly advantageous, further refinements. Preferably, the infrared measuring instrument has control equipment for interrupting the forced transport during an infrared measurement phase. With the interruption of the forced transport, a constant flow of test material can be assured. The whole of the test material column rests during the time of measurement, for example, for 3 to 30 seconds. After the measurement is completed, the whole of the product quantity, that is, with the consolidated test sample, is carried away. There is a flow of fresh product, so that the danger of a repeated measurement of the same sample (perhaps, because this sample has remained attached in the area of the sensor) is excluded. The forced transport contributes oustandingly to a problem-free functioning. The test sample is also pushed away with the slight displacement pressure that must be employed. As will still be explained, there is additional assistance if the forced transport is accomplished with vibration. In this case, the consolidated flour is loosened once again on renewed start-up of the vibration or the forced transport. It is advantageous to provide independent time elements for interrupting the forced transport for the cyclic consolidation of the material to be measured and for the release, as well as for controlling the infrared measurement phase. With this, the preparation for the measurement can be conducted optimally and the test sample can be stabilized for the infrared measurement. The measurement segment may advantageously have a tubular, closed form in the region of the sensor in such a manner, that a measurement tube is formed. The infrared measuring instrument should be attached to the measuring tube in such a manner, that the optical axis of the infrared measuring instrument is essentially perpendicular to the surface of the material to be measured. The best results are achieved if the controllable pressure mechanism (device for cyclically consolidating the material to be measured) is arranged on the measurement segment in the region of the sensor but opposite to it in such a manner, that the pressure mechanisms consolidate the material to be measured against the sensor, so that the best possible correspondence between the product and the sensor is produced. A clearly defined test surface, which moreover has a defined surface nature, is presented to the sensor.

Advisably, the pressure mechanisms are formed by a pressureproducing body, which is displaceable in the direction of the sensor and can be activated, preferably once more, by a pneumatic cylinder, the path and pressure of which can be adjusted. The pressure-producing body may however be a part of a magnetic coil, the path and force of which can be adjusted.

A further preferred development of the invention also consists therein that the pressure-producing body is constructed as a moveable spoon. Moreover, the spoon is preferably arranged tiltably and so that it can be moved by means of pneumatic or electric driving mechanisms against the sensor, essentially in the direction of the optical axis. The first attempts with a spoon shape produced very favorable results. In these attempts, the spoon was shaped like a soup spoon and its concave side (inner side of the spoon) was turned towards the sensor, so that the material to be measured was consolidated with the spoon against the sensor.

An advantageous further development of the invention also consists therein that the equipment for cyclically consolidating the material to be measured has inflatable pressure cushions, which are arranged on the measurement segment on the side opposite to the sensor. Preferably, the pressure cushion extends along the measurement segment and has a length, which is at least a multiple of the longitudinal dimension of the measurement area defined by the sensor.

Particularly good test results were obtained in attempts with a device in the form of a piston for cyclically consolidating the material to be measured, the pistons preferably being activated pneumatically or electrically. In this connection, the nature of the operating medium employed, whether it be compressed air, oil under pressure or electricity, is less important than the controllability of the path, time and pressure.

A most advantageous development of the invention furthermore consists therein that the measurement segment is constructed as a vibrating measurement segment, with which the forced transport can be ensured by means of the vibration.

The vibrating measurement segment is realized particularly advantageously as a by-pass to a main product stream and the vibrator, once again preferably, is suspended so as to oscillate like a bell in the interior of the measurement segment. At the same time, the vibration brings about a forced transport in the measurement segment. The vibrator, due to its bell-like shape, and the corresponding wall section of the housing form a metering gap at the lower end of the measurement segment.

Advantageously, the measurement segment is arranged on the overflow principle in a by-pass in such a manner, that a first partial stream of the main product stream flows under the influence of gravity in the measurement segment and the rest forms the main stream. The dosage rate of the vibrational transport is advantageously controllable in such a manner, that the feed rate in the measurement segment is greater than the controlled discharge due to vibrational transport. By these means, it is possible to achieve that the measurement segment is always full of slightly compressed (by the vibrational energy) test material.

Only after the flow of material has ceased, is the measurement segment emptied completely. It is then ready for the next measurement task. The state of fullness or emptiness of the measurement segment can be used by way of the same measuring equipment for controlling the installation, for example, for the task of locking the installation. In many cases, vibrational energy is used in the preparation of bulk samples for laboratory measurements. A first preparatory step is achieved by means of the particularly advantageous use vibration that has been described, and this step is then followed by the consolidation as a second step.

In a different advantageous refinement of the invention, the measurement segment has a preferably horizontal screw conveyor that ensures forced transport, back-pressure elements for the material to be measured being arranged at the end of the measurement segment. Preferably, a butterfly valve that opens under the transporting pressure or permanently installed wires or lamellas can be used as back-pressure elements, the equipment for cyclically consolidating the material to be measured, as well as the sensor, advisably being arranged in the region ahead of or between the screw conveyor and/or the back-pressure elements.

The solution with the screw conveyor is particularly useful for products with poor flowability of products, which tend to cake during vibration, such as products with a high fat content.

The invention furthermore relates to a process for the continuous quantitative determination of components, especially of protein and/or water, in floury or other groundable food products by means of infrared measurement.

Test data in industrial plants has meaning only if it can be used in conjunction with the measured product or the processing that is to be carried out.

Maintaining accurate protein and water contents, in flour for example, is frequently prescribed by law; in any case, however, it must be guaranteed in the trade. In contrast to a feed mill, in which the product to be worked up is passed directly and only once through the working-up process, the product in a flour mill must, in some cases, pass through repeated working-up processes. There are basically two ways of producing flour, intermediate forms also being possible, depending on the special features of the mill:

1. The grain is processed by means of an appropriate guidance system directly to the quality of flour desired by the purchaser, or
2. basic flour types are produced, which are mixed together at a later time to meet the quality requirements of the customer.

In both cases, however, the best possible control of the processing/cleaning/wetting/ grinding and sifting processes, etc., are a very important production requirement. With this, the direct controllability of the primary parameters becomes increasingly critical. Here also, the invention represents a decisive further step with respect to the control in the mill, in that the material to be measured, that is, for example, the flour, is measured not with a greater absence of cavities, but in a state, in which it is also deliberately consolidated additionally, and it is in this state that it is measured with infrared light.

The new process is characterized by the fact
that the material to be measured is passed over an infrared measurement segment, in which
a slight compression and smoothening of the groundable product is produced by the forced transport in the region of the sensor,
that the material to be measured is consolidated against the sensor during the measurement and irradiated with radiation, preferably in the infrared region, and
that the protein and/or water content (possibly the ash content and/or the color value) are determined by means of a measuring device and a computer from the radiation or light reflected diffusely from the consolidated test sample.

Depending on the application, the measurements can be repeated as often as is desired, preferably in a specified cycle.

In an advantageous continuation of the inventive concept, the test data obtained was used, on the basis of specified memory values and a second computer, directly for automatically controlling the raw material mixture and/or the addition of water and/or the flour mixture by controlling and regulating the mill with respect to the protein content and/or water content of the groundable product. This can be accomplished using one or more true control circuits for each of the factors given below:
protein—raw material mixture
water content—water addition
protein—flour mixture All values (such as the raw material mixture, water addition, protein content, flour quality, etc.) can be specified for the mill by means of an overriding computer. At the same time, the overriding computer can prescribe limiting values, within which the control circuits mentioned control and follow-up the settings for the operating facilities in question.

For example, if a "protein raw material mixture" control circuit is formed, (at least some of) the individual raw material qualities are treated separately up to the first grinding step, so that a correction can be made directly ahead of the grinding step (and therefore with the least possible time delay).

Correspondingly, it should be possible to add water immediately before the grinding step, so that at least smaller corrections are effective immediately (larger changes to the water addition must however be carried out in the main preparatory step ahead of the conditioning cell). Of course, in controlling the protein values as well as the water values, delays that arise out of the course of the grinding must always be taken into consideration.

In applying the inventive process to the flour composition, it is a question of a control process for issuing the necessary control and reversing commands towards a specific goal (reaching a nominal value). The same is true for the addition of gluten to flour.

It is possible to proceed correspondingly with respect to the values for the ash and color of the flour, even if, at the present time, no great importance is attached to controlling the mill with respect to ash and color values.

Due to the invention, further decisive progress in supervising and controlling the mill as a whole become possible, especially through the possibility of realizing
direct control of protein values
direct control of water values.

The inventive process can advantageously be developed further owing to the fact that a slight compression of the ground material for carrying out the measuring phase can be ensured by interrupting or stopping the forced transport and that the test sample is made ready and kept constant (unchanged) up to the measurement of all components (protein, water, ash, brightness) by mechanically consolidating the meaterial to be measured in the region of the sensor.

For reasons of foolproofness, it is particularly advantageous to repeat the measurement phases cylically at selectable time intervals. The frequency of the repetition depends on the particular circumstances of the handling process.

Furthermore, it is particularly appropriate to repeat, if possible, each individual measurement during a measurement phase, to average the test results of a group of measurement phases and to make these averages available as feedback values to the second computer for controlling or regulating the raw material mixture and- /or the water content and/or the flour mixture, and to adjust the product parameters to particular, specified values.

As further information, the invention also provides a measure of the uniformity of the mill run, it being possible to draw conclusions concerning possible sources of interference from a comparison of several values.

For example, the sudden addition of a few percent of wheat with an increased protein content can be printed out after a short time delay; this enables the operator to rapidly detect such a change, for example.

The invention furthermore relates to a process for monitoring the components of farinaceous foods or of groundable food products, in which the groundable product is irradiated with infrared light and the proportion of the individual components (materials contained) is determined from the measurement of the reflected intensity of the spectral regions assigned to the individual components (materials contained), in which the groundable product inventively is passed continuously over an infrared measurement segment and smoothed and consolidated on its irradiated surface for the measurements that continuously follow one another, the movement of the groundable product being stopped within the infrared measurement segment during each measurement and the light, reflected from the consolidated test sample, being evaluated for each measurement by means of a computer with regard to the reflected intensities of the desired spectral ranges, and the values for the components, so obtained, being compared in each case with a set value specified by a further computer, measures furthermore being taken or corrective signals being generated as a function of the deviations detected between the values determined and the values specified (for example for the raw material mixture, the flour composition, the water addition, the gluten addition, the specified settings for the grinding rollers, etc.).

In the following, the invention is explained in principle in greater detail by way of example by means of examples of the operations.

Figure 1:
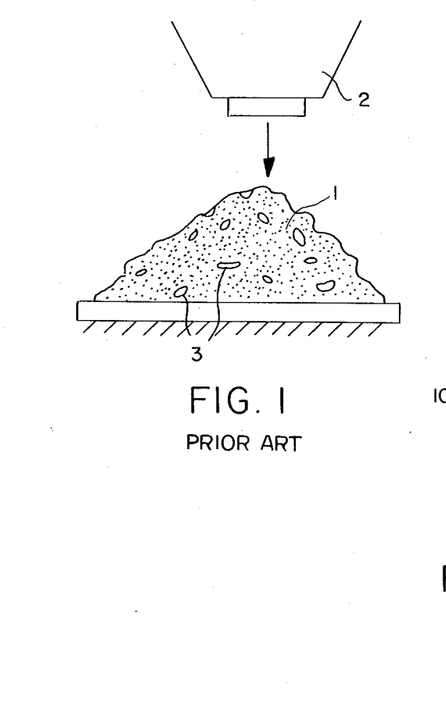
FIG. 1 shows a test sample corresponding to the state of the art.

FIG. 1 shows a small heap 1 of loose flour, onto which the infrared measurement optics 2 are directed. As can be seen, the material has a larger number of gas i.e. air cavities 3, so that, as experience has shown, a measurement with infrared radiation will provide inaccurate results. The irregular surface, as well as the uncontrollable air cavities distort the results, since the reflection is affected by the arbitrary position of the particles of the material at the surface as well as of the differently reacting gas or the air.

Figure 2:
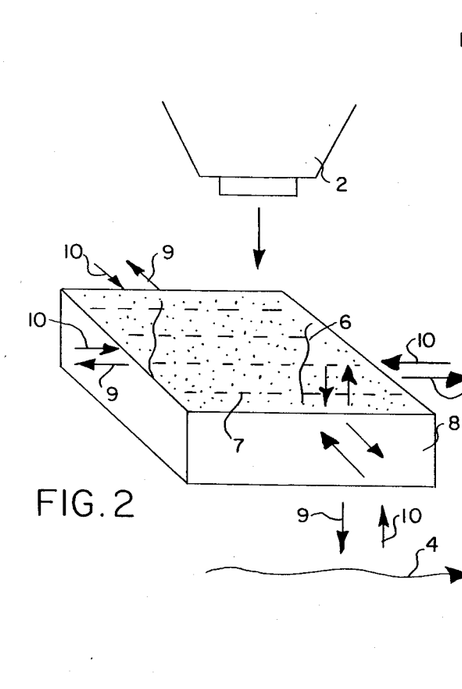
FIG. 2 a test sample from FIG. 1 after slight compression, for example, in a screw conveyor.
Figure 3:
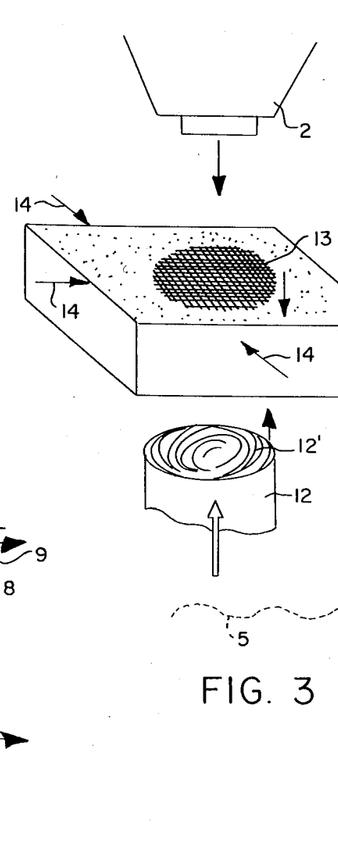
FIG. 3 schematically shows a test sample in the consolidated state of the invention.

The discoveries of the invention are shown by means of FIGS. 2 and 3, the product movement being indicated in both Figures by means of arrows 4 and 5 respectively. If the movement of the product is ensured by forced transport (for example, a screw conveyor), then the product is slightly compressed. Especially in the case of a screw conveyor, the transport by means of a screw conveyor can easily be adjusted so that the measurement segment is always filled with product. Preferably, the length of the housing for the screw conveyor is selected so that the end portion of the housing, in which there is no screw, is as long as the screw itself, so that a product plug must be pushed by the screw. Such an arrangement ensures that the product cannot escape from the measurement region and that the packing density cannot alter during the measurement. Stopping the transport then ensures that the test sample remains unchanged.

Floury materials have good air-holding capabilities. On compressing flour, the air contained therein is also compressed at the same time. When the screw conveyor is switched off, not only is the pressure on the flour removed, but the air contained in the flour can expand freely. By so doing, fine cracks 6 may develop and cavities may once again appear in the surface of the flour facing the infrared measurement optics 2. The density of the product only apparently remains the same. Depending on the particle composition that happens to exist, the surface of the flour, as formed by the forced mechanical transport and a more or less rough interior side of the housing, leads to grooves 7, which can have an interfering effect on the test results. Because of the considerably compressibility of flour, the nature of the test sample 8 is not constant without additional intervention. Since the expansion of the middle region of the flour plug does not extend to the two sides, that is, the product remains practically stationary in the region of the infrared measurement optics 2, this state of affairs is not recognized immediately. The product sample expands in all directions (see arrow 9), as a result of which the previous compression (direction of arrow 10) is largely cancelled once again.

These possible sources of error are now eliminated completely with the invention. In the measurement segment 24 (see FIG. 5 for example), that is, in the already precompressed material, an actual consolidation is produced, as is shown in FIG. 3. The material to be measured 11 is compressed by a piston 12 pneumatic piston 32 in FIG. 5 against the measurements optics 2. Moreover, not only is the flour consolidated, but air inclusions present are removed at the same time, since the air emerges from the region 13 of high pressure. The pressure region 13 has been hatched in order to indicate that an absolutely uniform surface can be formed for the purpose of measurement and maintained, until the measurement procedure is concluded. The arrows 14 are intended to indicate that the flour cannot escape to any of the sides, that is, it is kept spatially under pressure. The region of increased pressure is conical in shape and is formed on the basis of the mechanics of bulk materials. When the measurement is completed, the whole of the measured material 11 is pushed away. A new measurement can be repeated at any time (for example, cyclically).

Figure 4:
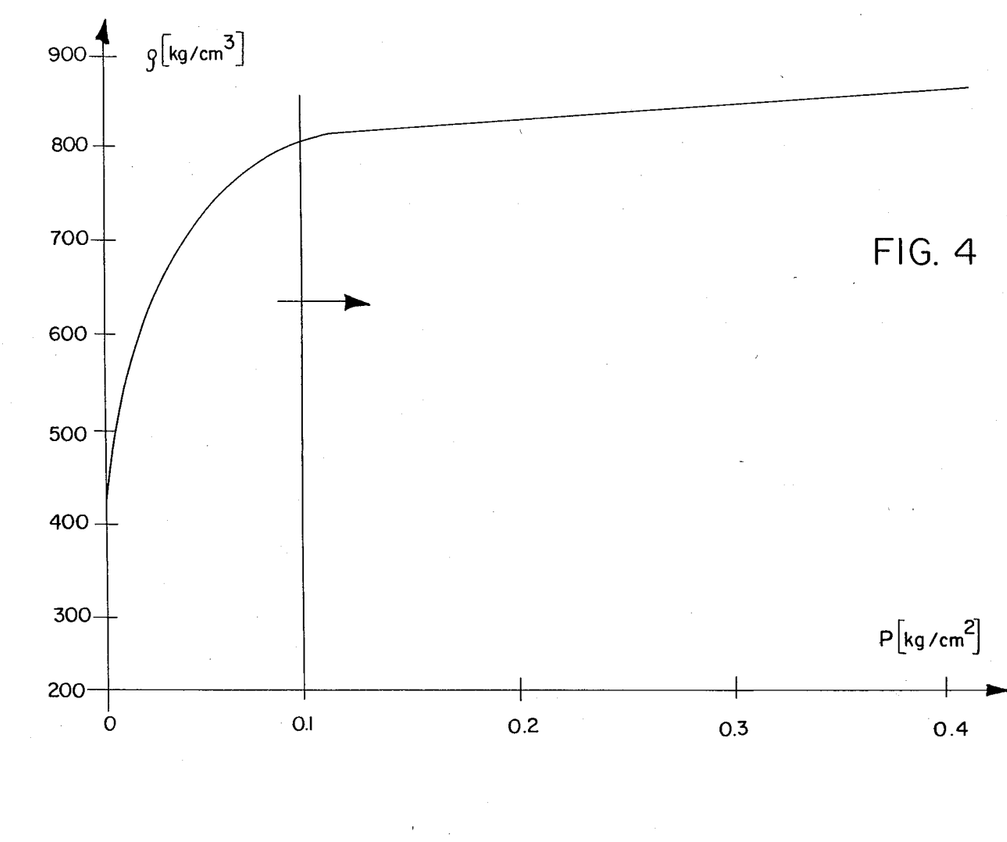
FIG. 4 shows the relationship of density kilograms per cubicc centimeter to varying pressure P kilograms per cubicentimeter for a flour sample.

FIG. 4 shows the pressure and compression behavior of flour. Inventively, the operating range for the consolidating pressure preferably is above 0.1 kg/cm² and especially above 0.4 kg/cm². The best results were obtained in the range from 0.4 kg/cm² to 1 kg/cm². Admittedly, even higher pressure may be chosen, but have the disadvantage that the product, in some cases, becomes lumpy; at very high pressures, the danger even exists that the flour itself will be damaged. In tests with good results, a pressure of 6 kg/cm² was used, in which case, however, the consolidating piston operated against a stop.

Figures 5, 5A:
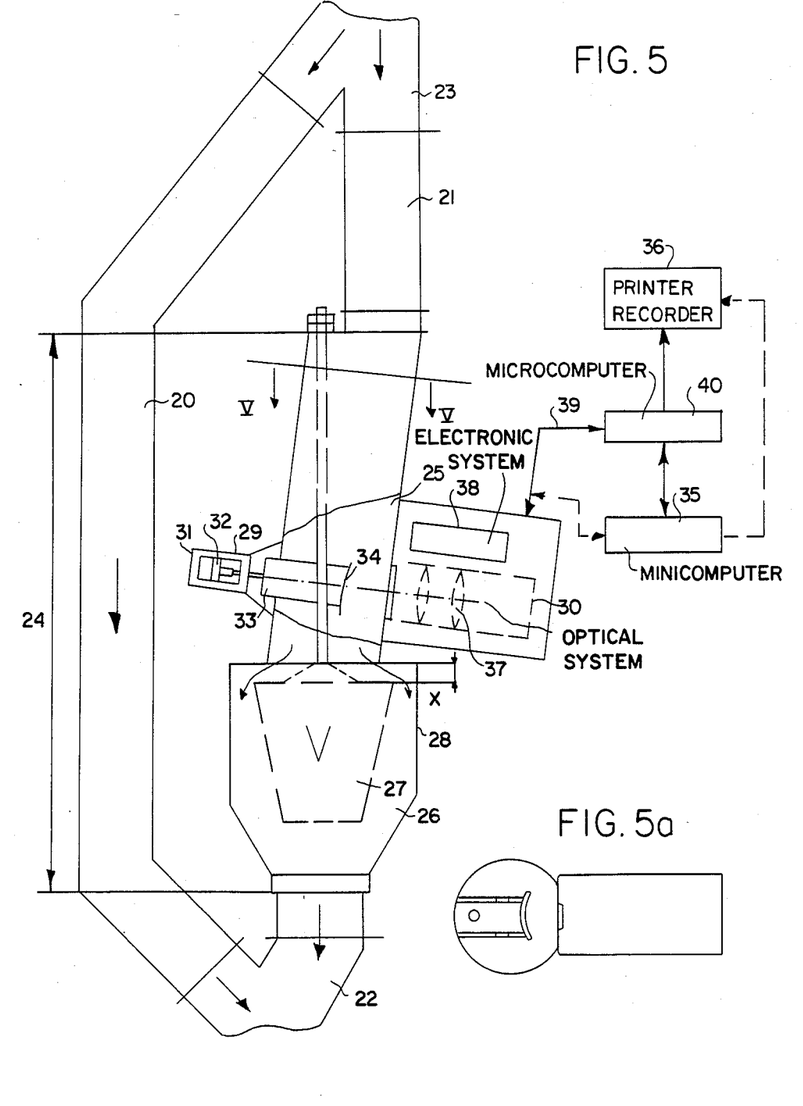
FIG. 5 shows a schematic representation of a section of an inventive attachment.
FIG. 5a shows the section V—V of FIG. 5.

FIG. 5 shows a complete measurement segment, or element, 24 of the invention. A main pipeline 20, in which the main product stream flows, is connected to a branch pipeline or by-pass 21, the end of which discharges once again over a length of pipe 22 into the main pipeline 20. A delivery pipe 23 represents the inlet connection between the main pipeline 20 and the by-pass 21. The measurement segment has an upper compression space 25, as well as a vibrating outlet 26, in which (there is) a vibrator 27, whose external boundaries at the top form an adjustable metering gap X with the housing 28 of the vibrating outlet 26. Moreover, the vibrator 27 is suspended in the housing 28 so as to oscillate. In the lower third of the compression space 25, equipment 25 for cyclically consolidating the groundable product as well as a sensor 30 are arranged. The pressure-producing mechanism of the equipment 29 comprise a pneumatic cylinder 31, a pneumatic piston 32, as well as a plunger 33, which, relative to the compression space, can be displaced along the axis of the pneumatic cylinder 31. The plunger 33 has a curved pressure surface 34, which is directed scoop-like against the sensor 30. In the sensor 30, there is an optical system 37, as well as an electronic evaluating system 38, from which the digital signals are passed over a standard interface to a microcomputer 40 or a minicomputer 35. Microcomputer 40 can be connected directly to a printer 36. The command unit for the whole of the measurement segment 24 is formed by the microcomputer 40, which controls the vibrator 27 and the pneumatic cylinder 31 by way of the electronic evaluating system 38 and, at the same time, prepares and initiates the measurement phase of the sensor 30.

Figures 6, 6A:
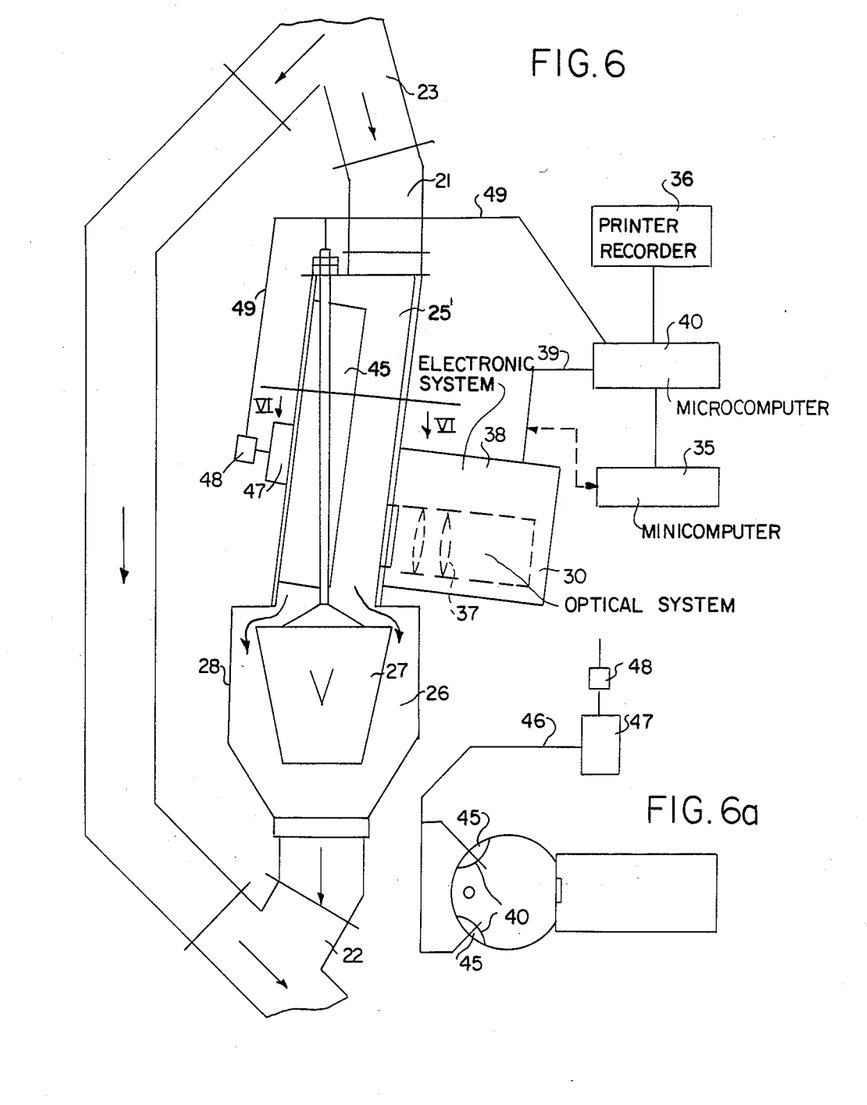
FIG. 6 shows a different embodiment of an inventive attachment with an air cushion as device for cyclically consolidating the material to be measured.
FIG. 6a the section VI—VI of FIG. 6.

In the representations of FIGS. 6 and 6a, the equipment for consolidating the material to be measured comprises two inflatable air cushions 45, which are arranged along and within the measurement segment 25'. The two air cushions 45 are fed over a branched pneumatic pipeline (see FIG. 6a) as well as over a pneumatic pressure transducer 47 and controlled over a control head 48, which is triggered by way of an electric control cable 49 from microcomputer 40, as is the vibrator 27. Here also, the microcomputer controls the whole of the measurement motion, analogously to the solution of FIG. 5.

Figure 7:
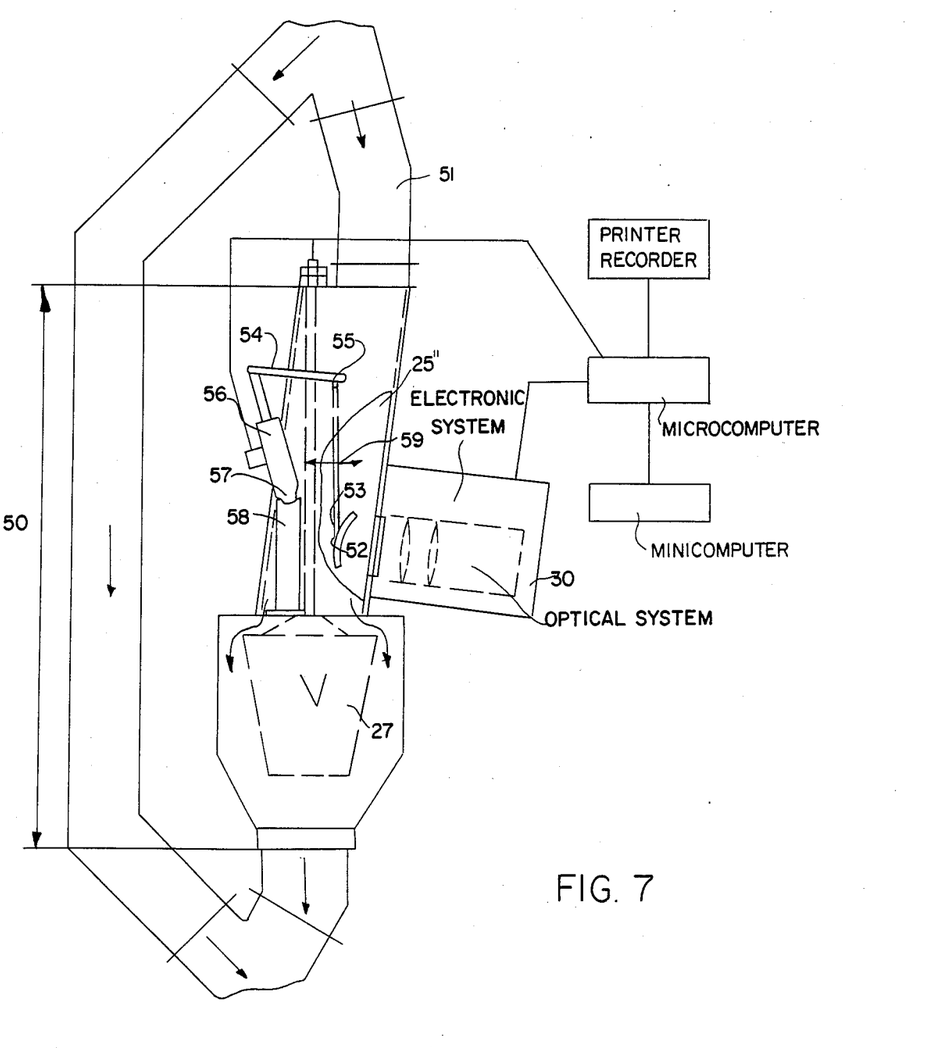
FIG. 7 shows a further embodiment of an inventive attachment with a spoon as device for cyclically consolidating the material to be measured.

The basic construction of the attachment shown in FIG. 7 essentially corresponds to that of the constructions shown in FIGS. 5 and 6; however, it has a different mechanical arrangement for consolidating the material to be measured in the region of the sensor 30. The measurement segment 50, shown in FIG. 7, is therefore somewhat modified relative to those of FIGS. 5 and 6. However, in all three examples of the operation of FIGS. 5, 6 and 7, the compression space 25, 25' and 25' respectively is constructed as a tubular housing. It is particularly important in the solution of FIGS. 5 and 7 that the compression space 25, 25' is somewhat enlarged towards the bottom. The cross sectional area of the measurement segment, which is formed here by the compression spce 25' therefore increases towards the bottom. Not only can the influence of wall friction on the product be reduced with such an arrangement, but a possible interfering effect of mechanical baffles in the compression space can also be excluded. In Fig. 7, the equipment for consolidating the groundable product comprises a spoon 52, which is arranged by means of a spoon handle 53 within the measurement segment 50 (that is, in the compression space 25') so that it can swivel about a horizontal axis 55. The spoon handle 53 is connected rigidly over the axis 55 with a lever 54 and is driven by a pneumatic cylinder 56, which, for the required swivelling motion, is mounted so that it can swivel about a bolt 57 by means of a bearing 52 to the measurement segment. The spoon 58 can therefore carry out a motion (arrow 59), analogous to that of the curved pressure surface 34 of FIG. 5. For the measurement, the spoon 52 is moved against the sensor 30 with the mechanism described, as a result of which the material to be measured is consolidated in front of the sensor 30. When the measurement is completed, the spoon 52 is removed once again from the sensor 30 by means of the control system and the vibrator is switched on. By these means, the consolidated material is loosened once again and discharged downwards.

Figure 8:
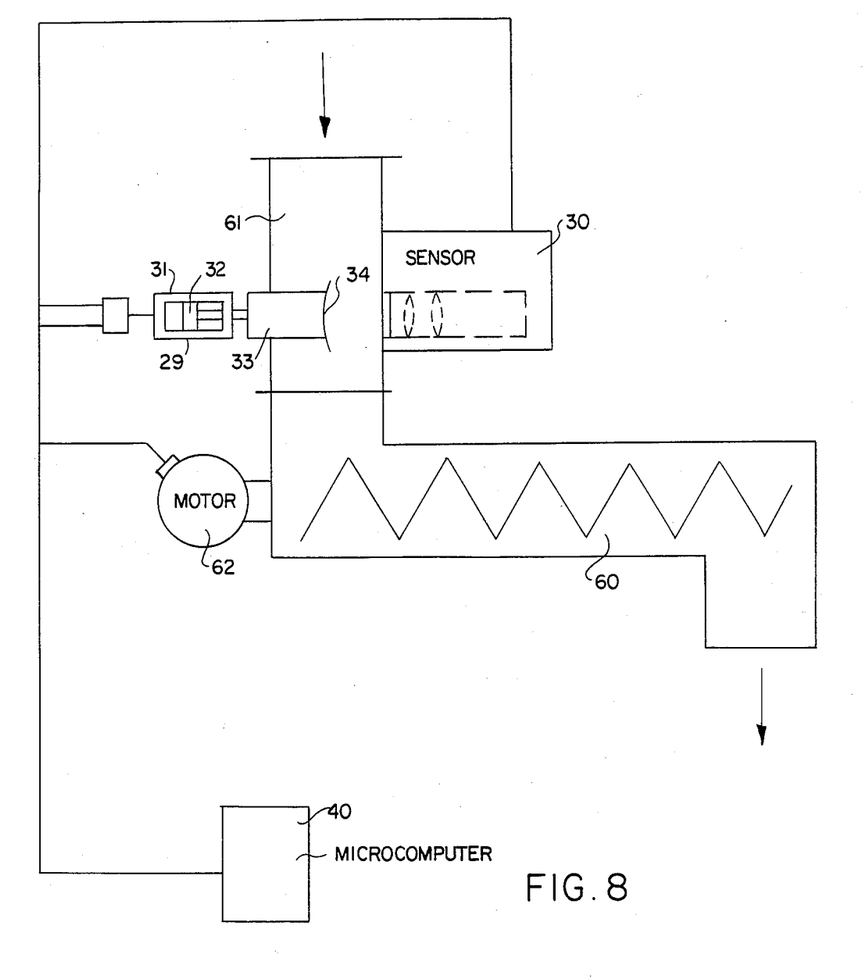
FIG. 8 is a schematic representation of an inventive arrangement with a pneumatic piston (as in FIG. 5), the unit being arranged above a screw conveyor.

In FIG. 8, the application of the invention measuring process is shown schematically in connection with the use of a metering screw or screw conveyor 60. The sensor 30, as well as the equipment for consolidating the material to be measured 29, 31, 32, 33 and 34 correspond to the showing in in FIG. 5. The solution with the spoon, as shown in FIG. 7, would, however, also be applicable here in view of the analogous movement imparted to the spoon 52 in FIG. 7. The screw conveyor 60 is controlled by mechanism (not shown) in such a manner, that the measurement space 61 is constantly filled with dearated product during normal operation. The sensor 30, the equipment for consolidating the product, as well as a drive motor 62 for the screw conveyor 60 are controlled by way of the microcomputer 40.

Figure 9:
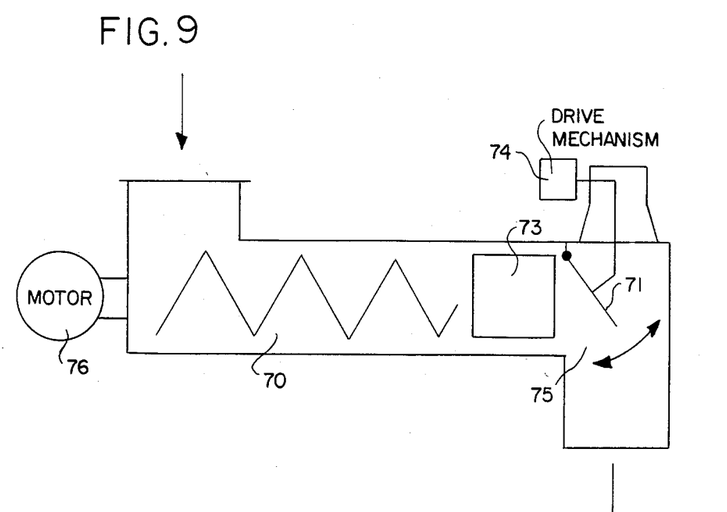
FIG. 9 shows a view and FIG. 10 a plan view of a further embodiment of the invention, in which the whole of the measuring attachment is arranged between a screw conveyor and back-pressure elements.
Figure 10:
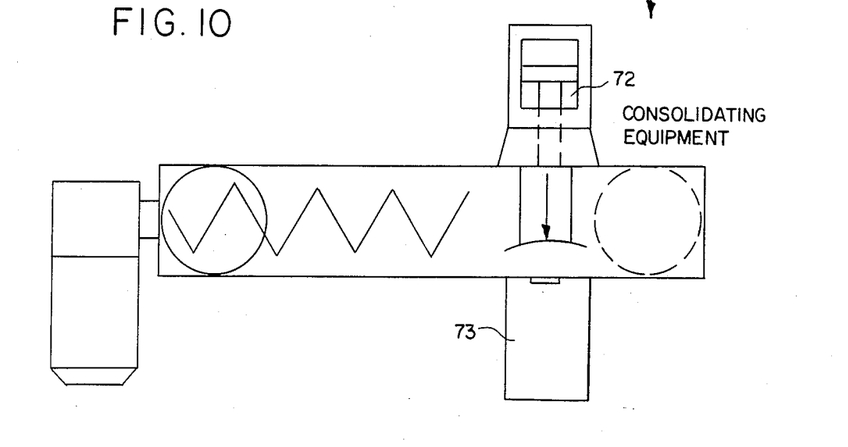

A form of construction, modified from that of FIG. 8, is shown in FIGS. 9 and 10, FIG. 9 being a schematic representation and FIG. 10 a plan view of the attachment of FIG. 9. In the region of the outlet beyond the sensor 73 screw conveyor 70 coorporates with a back-pressure element 71 which can be moved by driving mechanism 74 in the desired cycle and with the desired force against and away from the opening 75. A drive motor 76 and the driving mechanism 74 or the back-pressure element 71 are so matched to each other, that a particular pressure is maintained in the material to be measured for the measurement. The screw conveyor 70 works against pressure. In preparation for the measurement phase, this pressure is built up by positioning element 71 as shown in FIG. 7 and the equipment 72 (FIG. 10) for consolidating the material to be measured is activated. The desired test data is then recorded by sensor 73. When the measurement is completed back pressure element 71 is moved to an inoperative position whereby opening 75 is released once again and the continuous throughput of product is set in motion once again by switching on drive motor 76. From the above disclosure it will be appreciated that back pressure element 71 also acts as a valve.

Figure 11A:
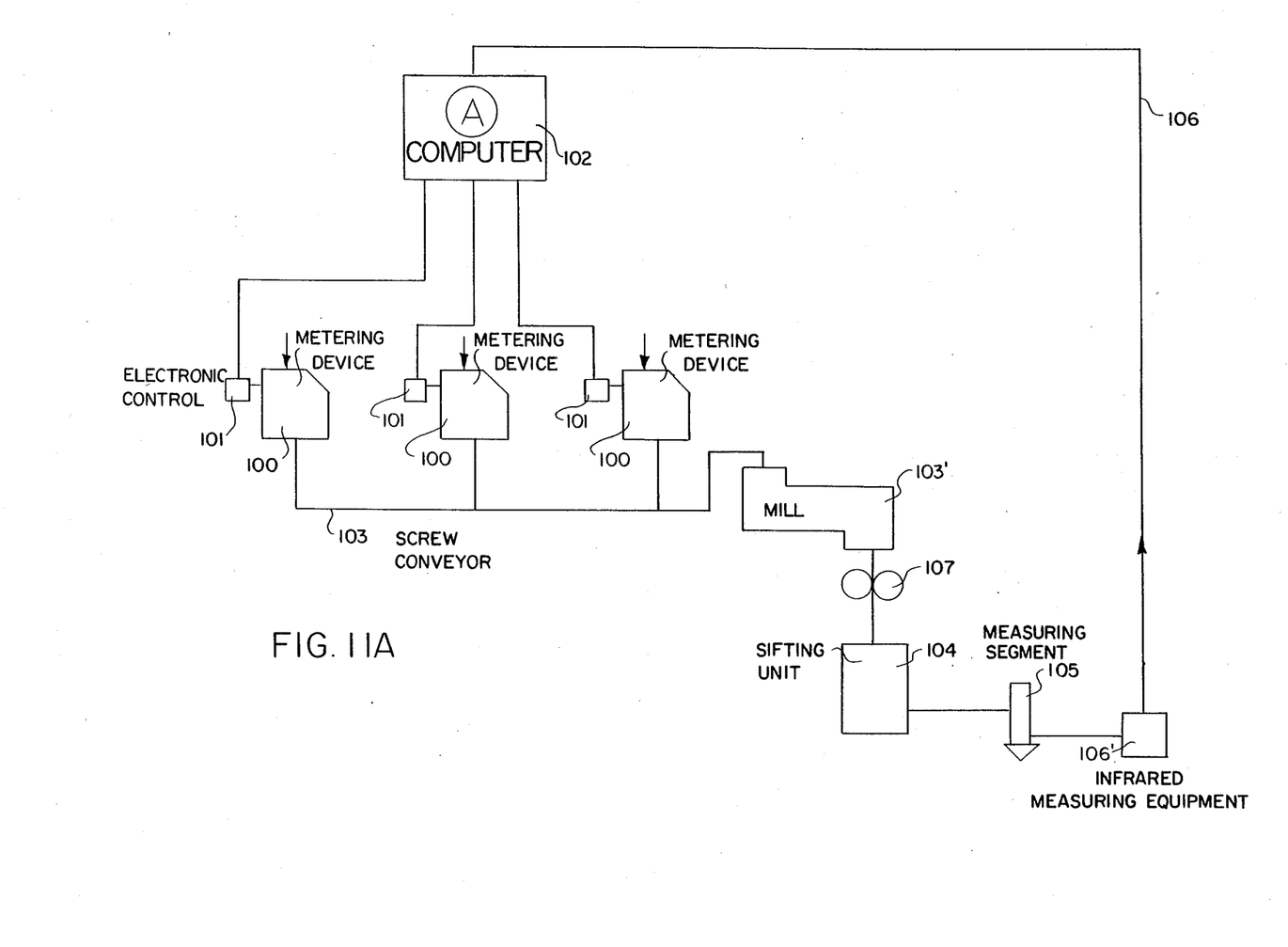
FIG. 11A schematically shows an inventive control system for mixing the raw material in a mill.

FIG. 11A shows a particularly advantageous application of the inventive measurement process for controlling and regulating the product mixture for the production of flour, grits and vapor in a mill.

For the particular product varieties stored, the quantitative ratios are set to the desired value by means of a computer 102 and a flow-through metering device 100 with an attached electronic control system 101. The product mixture is conveyed over a common screw conveyor 103 into the mill 103' and by means of cylinder mills 107 to the sifting units 104. The flour obtained is measured in a measurement segment 105 with respect to its components, for example, the protein content, and the values determined by infrared measuring equipment 106' are entered into the computer 102 over control lines 106. If now the computer 102 detects deviations from the desired (specified) set protein value, it automatically corrects the mixture until (taking the time delay that occurs into consideration) the desired, actual protein value agrees with the set value.

Figure 11B:
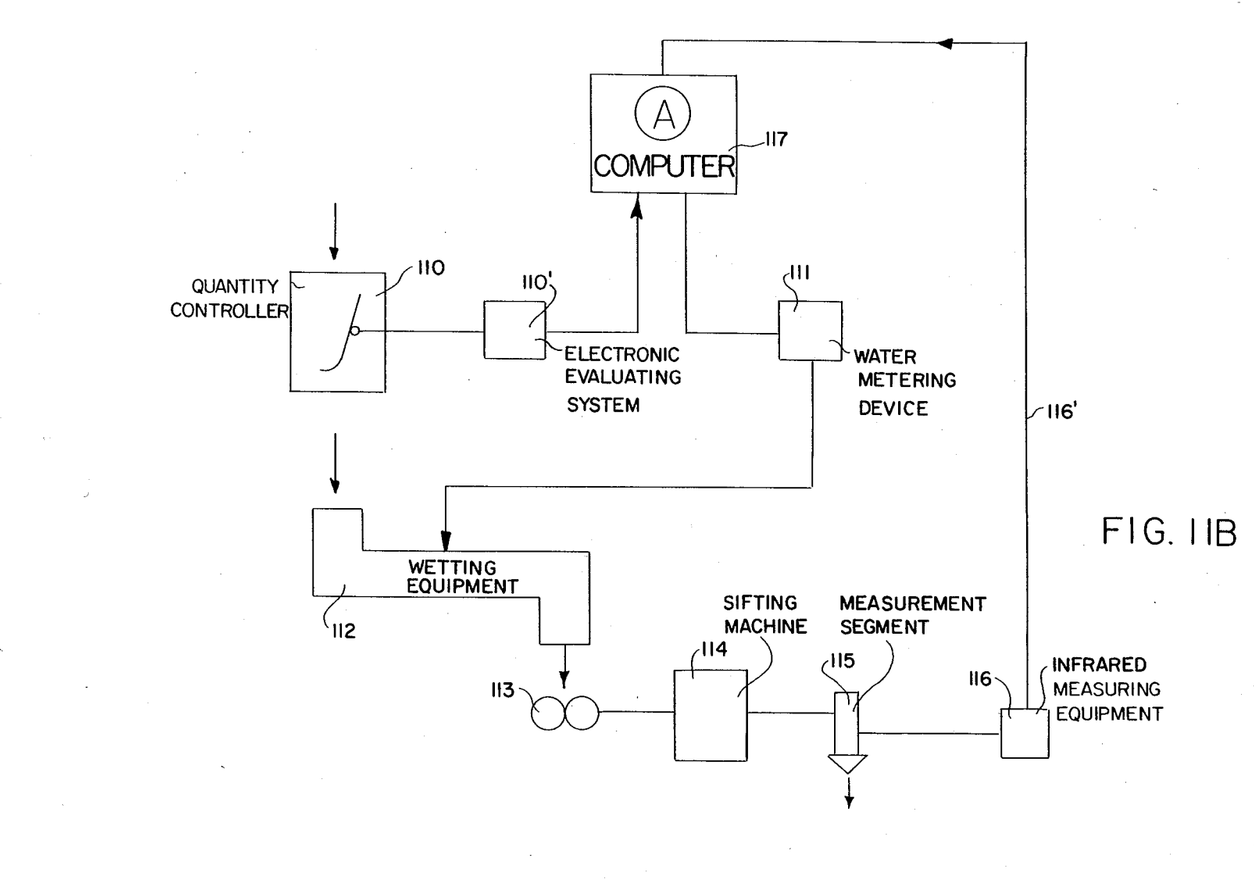
FIG. 11B shows an inventive control system for the addition of water in a mill (schematic).

The control system for the addition of water is shown in FIG. 11B in much the same way as it has been shown in FIG. 11A. The amount of crude product is measured continuously by an automatic quantity controller 110 and the amount of water, required for a desired set value, is metered in automatically over a water metering device 111. This quantity by means of an electronic evaluating system 110' is converted into physical signals supplied to computer 117. The raw material and the water are mixed in intensive wetting equipment 112 and ground in cylinder mills 113. The flour is sifted out in plan sifting machines 114 and the contents, in this case the water content of the flour, are measured in a measurement segment 115. The measurement signal of the infrared measuring equipment 116 is passed over a control line 116 to the computer 117, which compares the actual with the set value and corrects for deviations in accordance with a stored program by appropriately altering the water addition over the water metering device 111.

Figure 12:
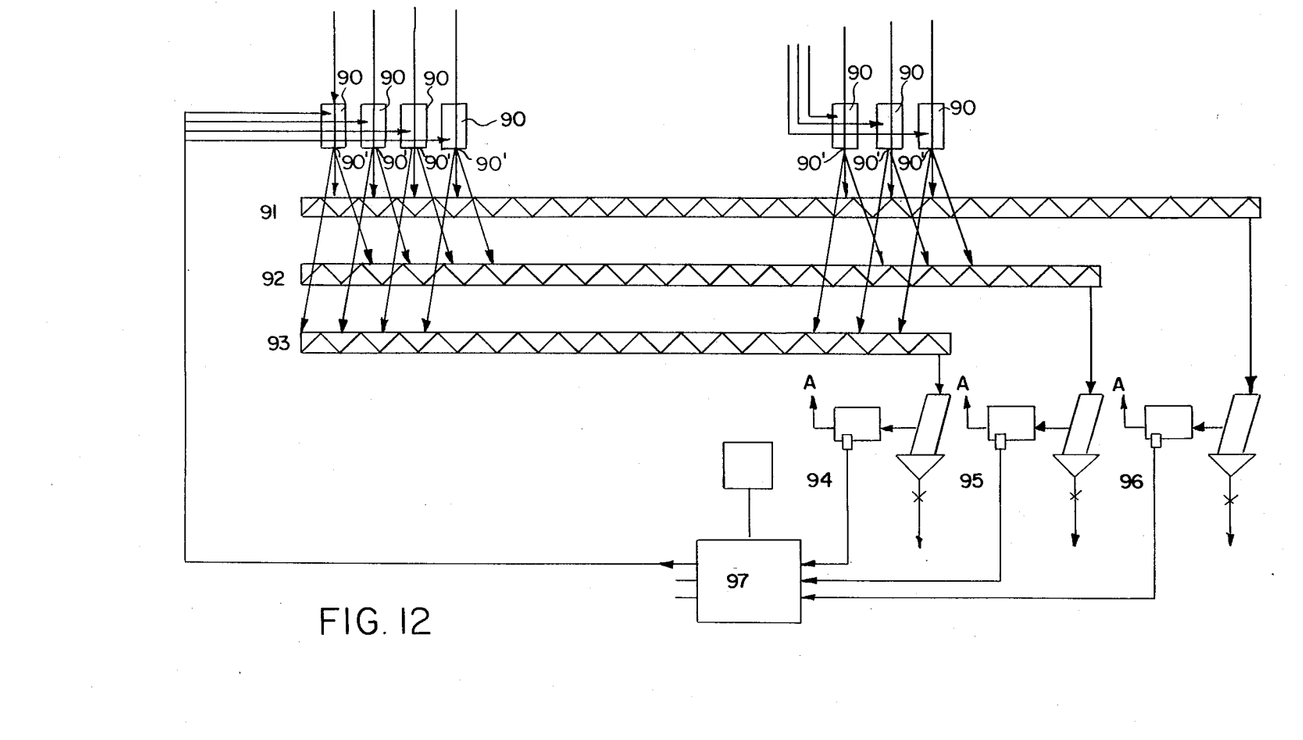
FIG. 12 schematically shows the inventive mixing of different flour qualities.

FIG. 12 shows a further interesting application of the new process for the production of a flour mixture, for which the desired values of the contents, for example, protein, ash and color, have been specified. Nozzles 90 represent the outlets of sifters, the outlet of which can be directed to one of three mixing screws 91, 92, 93.

On each of the nozzles 90, there is mounted a pipeline distributing guide 90', which is controlled by a computer 97 on the basis of the deviations between the desired set value and the actual value (measured value). A measurement segment 94, 95, 96 for determining the measured values is provided at each outlet of the mixing screws 91, 92, 93.

The inventive process for the first time also makes it possible to control the individual parameters in the roll crushing process, for example, the roller pressure, in that, for example, damage to protein can be monitored automatically by reducing the grinding pressure and appropriate control instructions can be given.

The equipment for consolidating the material to be measured can also, advantageously, have a spring-loaded or elastic element, for example in the region of the pressure surface 34 (FIG. 5), for keeping the consolidating pressure constant. Corresponding to this, the spoon handle 53 could be constructed as a spring-loaded element. By so doing, the pneumatic piston cn be operated against a stop and a residual pressure maintained by the remaining elastic force of the spring. With this procedure, the slight yielding of the consolidated product can be compensated for by an appropriate after running of the equipment for consolidating the material to be measured.

What is claimed is:

1. In an apparatus for continuously determining parameters of a particulate material product, such as flour or other finely comminuted food product, which apparatus includes a tubular feed line for the product and transport means for transporting and pre-compressing said product during its transport through said feed line, the improvement consisting in that the feed line includes a measuring element containing a sensor for infrared measurement, and further including consolidating means for consolidating said product in the region of said sensor for infrared measurement so as to enable determination of said parameters as a function of sensor response.

2. Apparatus as defined in claim 1, wherein said sensor is an infrared sensor whose output is supplied to control means for interrupting the operation of said transport means for the duration of an infrared measurement phase by said infrared sensor.

3. Apparatus as defined in claim 2, wherein said control means not only interrupts operation of said transport means to permit cyclic consolidation of the product, it also initiates and controls the infrared measurement phase.

4. Apparatus as defined in claim 3, wherein the sensor has an optical axis which is essentially perpendicular to the surface of the product whose parameters are to be determined.

5. Apparatus as defined in claim 1, wherein the consolidating means is arranged in the measurement element opposite the sensor so as to consolidate the product by moving it against the sensor.

6. Apparatus as defined in claim 1, wherein the consolidating means has a pressure-producing body, shiftable in the direction of the sensor.

7. Apparatus as defined in claim 6, wherein the pressure producing body comprises a pneumatic cylinder, the path and pressure of which can be adjusted.

8. Apparatus as defined in claim 6, wherein the pressure-producing body is constructed in form of a movable spoon.

9. Apparatus as defined in claim 8, wherein the spoon is movable by a drive means toward and away from the sensor essentially in the direction of an optical axis of the sensor.

10. Apparatus as defined in claim 9 wherein the spoon has a concave side facing the sensor.

11. Apparatus as defined in claim 1, wherein the consolidating means comprises an inflatable pressure cushion arranged in the measurement element opposite the sensor.

12. Apparatus as defined in claim 11, wherein the pressure cushion extends over a length of the measuring element, which is a multiple of the longitudinal dimension of a measuring area of the sensor.

13. Apparatus as defined in claim 1, wherein the consolidating means takes the form of an electrically or pneumatically activated piston.

14. Apparatus as defined in claim 1, wherein the transport means comprises a vibrator.

15. Measuring apparatus as defined in claim 14, wherein the vibrating measurement element is constructed as a bypass of a main pipeline.

16. Apparatus as defined in claim 14, wherein the measuring element has an enlarged housing part beyond said sensor in direction of movement of said product through said measuring element, the vibrator having a bell-like shape and being suspended to vibrate in the interior of the enlarged housing part for transport of said product and forming a metering gap at the lower end of the measuring element between the vibrator and a wall of the housing.

17. Apparatus as defined in claim 16, wherein the vibrational transport of product is adjustable so that the rate of feed of product into the measurement element is greater than the discharge therefrom such that the measuring element is constantly full of slightly compressed product occasioned by the vibration.

18. Apparatus as defined in claim 14, wherein an overflow of product is diverted from the main branch into the measuring element.

19. Apparatus as defined in claim 1, wherein the measuring element includes for said transport means a screw conveyor and a back-pressure element arranged beyond said sensor in direction of movement of said product.

20. Apparatus as defined in claim 19, wherein said back-pressure element comprises an openable valve for permitting movement of consolidated product through said feed line.

21. Apparatus as defined in claim 19, wherein the consolidating means as well as the sensor, are disposed ahead of the back-pressure element considering the direction of movement of said product.

22. Process for the continuous, quantitative infrared measurement of components, especially of protein and water, in floury or other finely comminuted food products, wherein the product is passed over an infrared measurement element formed in a feed line, a slight compression and smoothening of the product is produced by a forced product transport toward a region of an infrared sensor in the measurement element the product being consolidated against the sensor during measurement and infrared irradiation of the product in an infrared region of the measurement element such that at least one of the contents in the product comprising protein content, water content, ash content and color content is determined, with the aid of measuring equipment including computer means as a function of the output of the sensor sensing the product in the measurement element.

23. Process as defined in claim 22, wherein measured values for the protein content and water content of the product are compared by said computer means with stored values therein for automatic control of a raw material mixture for the product.

24. Process as defined in claim 22, wherein after said slight compression the forced transport of the product is stopped and during such stopping the product is consolidated by mechanical means and its contents measured.

25. Process as defined in claim 22, wherein the measurements of the contents of the product in the measurement element are cyclically repeated in predetermined time periods.

26. Process as defined in claim 22, wherein individual measurement results obtained during a measurement phase, optionally repeatable, are made available to the computer means for controlling mixture of said elements.

27. Process as defined in claim 22, wherein, while in each case one measurement phase is being put into effect, the consolidation of the ground material, which is stationary during the measurement phase, is kept essentially constant for the duration of the measurement.

28. Process as defined in claim 22, wherein the product is mechanically consolidated after said slight compression.

29. Process as defined in claim 22, wherein several measurements are made for each component during a measurement phase, an average of said measurements being compared with a predetermined value to provide a correction signal fed to said computer means for correcting the relevant contents of the product.

30. Process as defined in claim 22, wherein the measurement results from a number of individual measurement phases are averaged, and the average is supplied as an actual value to further computer means.

31. Process for maintaining the components of farinaceous foods or comminuted food products, in which the product is irradiated with infrared light and the proportions of individual components thereof is determined from measurement of reflected intensity of spectral regions of the individual components of the product, wherein the product is transported through an infrared measurement segment and smoothed and consolidated so as to present an irradiated surface for measurement of said reflected intensity of said spectral regions of the individual components of the product, movement of the product being interrupted within said infrared measurement segment during each sequential measurement, light reflected from the consolidated product being evaluated for each measurement by means of a computer means in relation to the reflection intensity of a desired spectral range, the values for the components thus obtained being compared with predetermined values stored in further computer means, corrections of value being made as a function of undesired deviations between the obtained values and the predetermined values.

* * * * *